(12) United States Patent
Starkey

(10) Patent No.: US 10,085,816 B2
(45) Date of Patent: Oct. 2, 2018

(54) COLLECTING AND HARVESTING CUT BONE FROM KERRISON RONGEUR

(71) Applicant: H & M INNOVATIONS, LLC, Wilmington, NC (US)

(72) Inventor: Michael Morgan Starkey, Kent, OH (US)

(73) Assignee: H & M INNOVATIONS, LLC, Wilmington, NC (US)

( * ) Notice: Subject to any disclaimer, the term of this patent is extended or adjusted under 35 U.S.C. 154(b) by 324 days.

(21) Appl. No.: 15/151,726

(22) Filed: May 11, 2016

(65) Prior Publication Data
US 2017/0325908 A1 Nov. 16, 2017

(51) Int. Cl.
| | | |
|---|---|---|
| *B29D 99/00* | (2010.01) | |
| *A61B 90/70* | (2016.01) | |
| *A61B 17/16* | (2006.01) | |
| *B29C 45/14* | (2006.01) | |
| *B65D 1/10* | (2006.01) | |
| *B29L 31/56* | (2006.01) | |

(52) U.S. Cl.
CPC .......... *A61B 90/70* (2016.02); *A61B 17/1604* (2013.01); *A61B 17/1635* (2013.01); *B29C 45/14336* (2013.01); *B29D 99/0096* (2013.01); *B65D 1/10* (2013.01); *B29L 2031/565* (2013.01)

(58) Field of Classification Search
CPC .......... B29D 99/0096; B29C 45/14336; B29L 2031/565; A61B 90/70; A61B 17/1604; A61B 17/1635
See application file for complete search history.

(56) References Cited

U.S. PATENT DOCUMENTS

| | | | |
|---|---|---|---|
| 2014/0165309 A1 | 6/2014 | Frey et al. | |
| 2014/0319135 A1* | 10/2014 | Fox | B29D 99/0096 220/202 |
| 2014/0364961 A1 | 12/2014 | Mikhail et al. | |
| 2015/0282816 A1 | 10/2015 | Hensler et al. | |
| 2016/0354179 A1 | 12/2016 | Hensler et al. | |

FOREIGN PATENT DOCUMENTS

| | | | |
|---|---|---|---|
| WO | WO 2009054968 A1 | 4/2009 | |
| WO | WO-2012130916 A1 * | 10/2012 | B29C 45/1635 |

OTHER PUBLICATIONS

International Search Report and Written Opinion in PCT/US2017/032054 by the USPTO, dated Jul. 26, 2017, 10 pages.

* cited by examiner

*Primary Examiner* — Robert B Davis
(74) *Attorney, Agent, or Firm* — Tillman Wright, PLLC; Chad D Tillman

(57) ABSTRACT

A collector includes a container body defining an interior containment space and having an open end for access, and a cap in covering relation to the open end and having an opening for receiving therein a distal end of a kerrison-type rongeur. An improvement includes the cap including a first plurality of scrapers in the form of fingers for engaging and dislodging cut bone from the cutting area of the distal end of the rongeur and a second plurality of scrapers in the form of wipers for engaging and dislodging cut bone from the cutting area of the distal end of the rongeur when the distal end of the rongeur is withdrawn through the opening from the collector, the second plurality being arranged so as to permit insertion of the distal end of the rongeur through the opening into the collector without engaging the distal end of the rongeur.

20 Claims, 20 Drawing Sheets

6002

6002

6002

6002

6002

6002

COLLECTING AND HARVESTING CUT BONE FROM KERRISON RONGEUR

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

COMPUTER PROGRAM LISTING

Submitted concurrently herewith via the USPTO's electronic filing system, and incorporated herein by reference, are one or more computer program files of the computer program listing of the present application. A table setting forth the name and size of each file included in the computer program listing is included below.

| File Name | Creation Date | File Size (bytes) |
| --- | --- | --- |
| ascify.txt | 5/10/2016 8:44 | 37473 |
| drawing.txt | 5/10/2016 8:44 | 1343316 |
| readme.txt | 5/10/2016 8:44 | 2593 |

One of these files, "readme.txt", contains instructions for extracting information from another of the files, "drawing.txt". This other file represents a compressed binary file that has been converted to ascii format. This file can be converted back to a compressed binary file utilizing assembly conversion program source code contained in the file "ascify.txt". The readme file includes instructions for compiling and running this conversion program source code, and instructions for converting the "drawing.txt" to the compressed binary file. The compressed binary file comprises a .zip archive including one or more eDrawings files representing one or more computer models that can be opened using the publicly available eDrawings software from SolidWorks.

BACKGROUND OF THE INVENTION

The present invention generally relates to the collection of cut material from a rongeur and, in particular, the collection of bone from a kerrison rongeur. The following patent applications and patent application publications relate to the same subject matter: U.S. provisional patent application 61/975,698, U.S. patent application Ser. No. 14/679,903 and corresponding U.S. patent application publication no. 2015/0282816 A1; and international patent application PCT/US15/24402 and corresponding publication WO 2015/154060. Each of these applications and publications is incorporated by reference herein.

As discussed in these incorporated references, rongeurs are surgical instruments for the cutting away of human tissue, and most commonly, cartilage and/or bone. "Kerrison" rongeurs are utilized in spinal surgery to remove bone and to thereby gain access to the spinal canal, and rongeurs are well-known within conventional medical knowledge. Patent references disclosing and discussing kerrison rongeurs and their use in surgery include U.S. Pat. Nos. 3,902,498; 5,026,375; 4,722,338; 4,777,940; 4,777,948 and U.S. patent application publication 2003/0216740.

With reference to FIG. 1a of incorporated U.S. patent application publication no. 2015/0282816 A1 (hereinafter "the '816 Publication"), an exemplary prior art kerrison rongeur is illustrated. The kerrison rongeur includes a first jaw member 10 that slides parallel to line A relative to, and on top of, a second jaw member 20. The first jaw member 10 included a distal cutting end having a cutting edge 15. The second jaw member 20 includes a stop 40 for placement beneath the tissue to be cut, which is generally bone or cartilage. A cutting area 30 is defined between the cutting edge 15 of the first jaw member 10 and the stop 40 of the second jaw member 20. The first jaw member 10 includes an open, interior cross-section defining an enclosed area within which the bone tissue is received when cut. Such an exemplary cross-section is illustrated in FIG. 1B of the '816 Publication. As illustrated, the cross-section of the first jaw member 10 has a generally inverted U shape.

In an exemplary use of a kerrison rongeur, a surgeon places the bone to be cut, such as the leading edge of the lamina of a vertebra, within the open portion of the distal end of the rongeur. The surgeon then squeezes the handle of the rongeur, which advances a moveable jaw member of the rongeur through and amputates a portion of bone. A surgeon may wait until the jaw member becomes full of bone, at which time the rongeur must be completely removed from the surgical site and passed to a scrub nurse or assisting technician for bone removal. The removal from the instrument of the cut portion of bone often requires that the scrub nurse or assisting technician use a small rigid hook, or toothed forceps, and often further requires that the physician temporarily relinquish the instrument entirely to make such bone removal possible. Once cleaned, the instrument is returned to the surgeon who, in returning it to the surgical site, must then reorient himself to the task at hand. This sequence must then be repeated over and over again. Moreover, in a typical spinal fusion, this sequence may require as many as 50 to 100 such repetitions.

Alternatively, a surgeon may present the distal end of the rongeur to a scrub nurse or assisting technician after each cut for removal of the bone, thereby avoiding bone build-up within the jaw member of the rongeur. This can be done without the surgeon relinquishing the rongeur and without the surgeon removing his or her attention and focus from the surgical site. Conventionally, the scrub nurse or assisting technician manually swipes the end of the kerrison rongeur with a sterile material for removing the cut bone. The scrub nurse or assisting technician may repeat the swiping of the cut bone multiple times before harvesting the swiped bone from the material used to perform the swiping. A gauze sponge may be used for swiping. Rather than swiping the bone from the rongeur, a gloved hand may be used by the scrub nurse or assisting technician to directly remove the bone from the rongeur. Thereafter, the harvested bone from the patient may be used in the surgical procedure on the patient, e.g., in autografts.

The '816 Publication discloses various apparatus and methods providing a safe, expedient, and efficient way for the cut bone to be removed from the kerrison rongeur and harvested by a scrub nurse or assisting technician. One or more aspects of the present invention improve upon one or more such apparatus and methods of the '816 Publication.

SUMMARY OF THE INVENTION

The present invention includes many aspects and features. Moreover, while many aspects and features relate to, and are described in, the context of collection of bone from a kerrison rongeur, which is preferred, the present invention is not limited to only such use, as will become apparent from the following summaries and detailed descriptions of aspects, features, and one or more embodiments of the present invention.

In an aspect of the invention, a collector used to collect cut bone comprises: a container body defining an interior containment space for receiving and retaining collected bone and having an open end for access and removal of collected bone from the interior containment space; and a cap in covering relation to the open end. The container may comprise a visibly transparent material and may include graduations to indicate volume of collected matter in the container. The cap comprises an opening for receiving therein a distal end of a kerrison-type rongeur; a first plurality of scrapers in the form of fingers for engaging and dislodging cut bone from a cutting area of the distal end of the rongeur when the distal end of the rongeur is received within the collector; and a second plurality of scrapers in the form of wipers for engaging and dislodging cut bone from the cutting area of the distal end of the rongeur when the distal end of the rongeur is withdrawn through the opening from the collector, the second plurality of scrapers being arranged so as to permit insertion of the distal end of the rongeur through the opening into the collector without engaging the distal end of the rongeur.

The first plurality of scraper may be in the form of a brush disposed on the underside of the cap facing the interior of the container. The brush may comprise plurality of bristles which may comprise individual monofilament bodies. Moreover, the bristles may comprise a material that is absorbable by the human body, as it is believed that a bio-absorbable bristle is beneficial in the event that a bristle becomes dislodged and mixed with the harvested matter from the tip of the kerrison rongeur, and thereafter is inadvertently introduced into a patient.

In a feature of this aspect, the opening is configured to allow the passage of the tip of a kerrison rongeur of multiple sizes along with bone and other tissue matter carried on the tip.

In a feature, the scrapers of the first and second pluralities extend downwardly from an underside of the cap.

In a feature, the opening is located on a first side of the cap, and wherein the first plurality of scrapers extends downwardly on an opposite side of the cap relative to the opening.

In a feature, each of the first plurality of scrapers includes a proximate portion relative to the underside of the cap and a distal portion relative to the underside of the cap, the proximate portion being less flexible than the distal portion in engaging and dislodging cut bone from the cutting area of the distal end of the rongeur.

In a feature, the first plurality of scrapers forms a bristle field.

In a feature, each of the first plurality of scrapers extend from an underside of the cap toward the interior containment space.

In a feature, the opening is located in the cap.

In a feature, the opening is located on a side of the cap.

In another aspect, a handheld collector used to collect cut bone from a kerrison rongeur comprises: a cap; and a container. The cap comprises an opening dimensioned to receive there through a distal end of a kerrison rongeur. The container of the collector comprises a generally elongate body that is cylindrical in shape, and walls of the body define an interior containment space of the container into which bone falls when dislodged from the distal end of a received kerrison rongeur. The cap includes at least two distinct areas of different pluralities of scrapers for dislodging bone from the distal end of a kerrison rongeur.

In a feature, the cap is generally circular at a lower perimeter thereof and the opening extends an arc having an obtuse angle along the perimeter. The opening in the cap preferably is wide with respect to a diameter of the cap, and the arc preferably has an angle of between 130 degrees and 140 degrees.

In a feature, the cap is attached to the container in an upper portion of the collector and is removable from the container.

In a feature, the cap is attachable to the container by way of threads on both the container and the cap, whereby the cap screws onto the container. In particular, the cap comprises a threaded portion that engages and mates with a threaded portion of the container when the cap and container are screwed together.

In a feature, a gap extends between the different areas.

In a feature, a first plurality of scrapers similar or the same to each other is located in a first area of the underside of the cap, which first area is in close proximity to the opening, and a second plurality of scrapers similar to each other is located in a second area of the underside of the cap, which second area is further from the opening than the first area. The first and second areas preferably are arranged in spaced relation to each other such that a gap comprising an absence of scrapers extends between the first plurality and the second plurality of scrapers. Furthermore, preferably each scraper of the first plurality comprises a finger insofar as each scraper comprises a protuberance that is elongate with generally oval cross-section; each such finger has a stepped diameter between a proximal portion thereof and a distal portion thereof relative to the underside of the cap; and each scraper of the first plurality comprises a larger width at a proximal portion thereof and a smaller width at a distal portion thereof. The width of each scraper of the first plurality may taper along the proximal portion, decreasing as a height-wise extent increases in a direction away from the underside of the cap; the width of the distal portion may taper along the proximal portion, decreasing as a height-wise extent increases in a direction away from the underside of the cap; or both.

In a feature, the width of each scraper of the first plurality tapers along its overall height from the underside of the cap to its distal end. Alternatively, the width of each scraper of the first plurality does not taper along its overall height from the underside of the cap to its distal end.

In a feature, the first area of the first plurality of scrapers comprises a grouping of the scrapers that collectively form a bristle field.

In a feature, each scraper of the second plurality comprises scraper is seen to comprise a wiper having a length and a height that substantially exceeds a width thereof.

In a feature, the second area of the second plurality of scrapers comprises a grouping thereof collectively forming an arrangement of teeth.

In a feature, the second area of the second plurality of scrapers comprises a grouping thereof collectively forming a row of teeth, with each tooth being a wiper and with a gap extending between adjacent teeth. The row of teeth preferably is arranged along an arc generally extending in close relation to a circumferential boundary of the underside of the cap, and the second area of the second plurality of scrapers preferably comprises a grouping thereof collectively forming a single row of teeth. In other variations, the second area of the second plurality of scrapers comprises a grouping thereof collectively forming multiple rows of teeth.

In a feature, each scraper of the first plurality is more than twice the height of each scraper of the second plurality in extending away from the underside of the cap. Preferably the height of the lower portion of each scraper of the first plurality is greater than the overall height of each scraper of the second plurality.

In a feature, each scraper of the first and second pluralities is sufficiently rigid so as to generally hold form when not engaged by a distal end of a kerrison rongeur and to generally dislodge bone found in a cutting area of a kerrison rongeur when the scraper is moved into or through the cutting area.

In a feature, each scraper of the first and second pluralities is sufficiently flexible and resilient so as to generally deflect and bend—to various extents—upon abutment by and engagement with the distal end of a kerrison rongeur.

In a feature, each scraper of the second plurality is less flexible and resilient when compared to a proximal portion of each scraper of the first plurality.

In a feature, each scraper of the second plurality is less flexible and resilient when compared to a distal portion of each scraper of the first plurality.

In a feature, a proximal portion of each scraper of the first plurality is less flexible and resilient when compared to a distal portion of each scraper of the first plurality.

In a feature, each scraper of the second plurality, and the proximal portion and the distal portion of each scraper of the first plurality, together are all formed from the same material by molding.

In a feature, each scraper of the second plurality, and a proximal portion and a distal portion of each scraper of the first plurality, together are all formed from the same material by injection molding.

In a feature, the scrapers of the first plurality and the second plurality are integrally formed as a single component of the cap. Preferably the first component extends through a plurality of channels formed in a second component of the cap which channels extend between an underside of the cap and a topside of the cap; the first component comprises a topside portion located within a recess formed in a top surface on the topside of the second component; and the topside portion comprises an ornamentation including branding or a decorative element.

In another aspect, a method of manufacturing a cap for a collector—the cap comprising pluralities of scrapers that differ based on flexibility and resiliency as well as arrangement and spacing between adjacent scrapers, comprises the steps of: providing a base component; and injection molding an additional component onto the base component to form the cap, the additional component being molded in a shape defining a first area having a first plurality of scrapers defining a bristle field and a second area having a second plurality of scrapers defining a row of teeth, with a gap comprising an absence of scrapers extending between the first and second areas.

In a feature, the method of providing the base component comprises first molding the base component.

In a feature, the first component is overmolded on the base component.

In a feature, one or more of the base and additional components are molded from one or more inert plastic materials.

In a feature, the material from which the base component is molded comprises a bio-absorbable material.

In a feature, each of the first plurality of scrapers protrude at least twice the extent to which each of the second plurality of scrapers protrude.

In a feature, portions of the additional component extend through channels in the base component of the cap, the channels extending between a topside and an underside of the cap. Preferably first and second portions of the additional component respectively extend on opposite sides of the base component, the first portion of the additional component forming the first and second pluralities of scrapers. The scrapers preferably are permanently affixed to the base component on the underside of the cap and are not removable from the cap without tearing of the additional component.

In another aspect, a collector comprises a container and a cap, wherein the cap comprises pluralities of scrapers that differ based on flexibility and resiliency as well as arrangement and spacing between adjacent scrapers.

In a feature, a first plurality of scrapers each is shaped and configured in an arrangement to resemble a bristle field like that of a brush; and wherein a second plurality of scrapers each is shaped and configured in an arrangement to resemble a row of teeth, with the row of teeth extending along an opening in the cap, with the bristle field located distal to the opening, and with a gap extending between the row of teeth and the bristle field.

In a feature, the distal end of the rongeur is inserted through the opening in the cap without engaging any of the second plurality of scrapers.

In a feature, the distal end of the rongeur is inserted through the opening in the cap at an angle of between about 30 degrees and about 40 degrees.

In a feature, the first plurality comprises fingers.

In a feature, the first plurality of scrapers forms a bristle field.

In a feature, each of the second plurality of scrapers is in the form of a tooth.

In a feature, the second plurality of scrapers are arranged so as to form a row of teeth extending from the underside of the cap proximate the opening in the cap.

In a feature, each of the first plurality of scrapers comprises a bio-absorbable material.

In a feature, each of the second plurality of scrapers comprises a bio-absorbable material.

In another aspect, a kit comprises an aforementioned collector and a rongeur, wherein the collector is configured to collect cut bone from the rongeur of the kit.

Another aspect comprises a method of using an aforementioned collector to collect cut bone. In another aspect, a method of collecting cut bone from a kerrison rongeur using a collector—the collector comprising a container having an interior containment space for catching bone and a cap attached thereto in covering relation over the interior containment space, comprises the steps of: inserting through an opening in the cap of the collector a distal end of a kerrison rongeur carrying matter cut from a patient; and dislodging the matter from the kerrison tip whereby the matter falls into the interior space of the container and is thereby collected, by (a) causing the distal end of the kerrison rongeur to engage and be moved and rotated in engagement with scrapers of a first plurality of scrapers, each of the first plurality extending from an underside of the cap for dislodging bone from the kerrison rongeur, and (b) withdrawing the distal end of the kerrison rongeur from the cap while engaging the distal end of the kerrison rongeur with scrapers of a second plurality of scrapers, each of the second plurality extending from an underside of the cap proximate a perimeter of the opening for dislodging any remaining bone from the kerrison rongeur, a gap comprising an absence of scrapers extending between the first and second pluralities of scrapers. The kerrison rongeur thereafter is removed from the collector for further use. Later when the harvested matter is needed, the cap is unscrewed from the container and the matter, i.e., bone in preferred implementations, is retrieved from the container.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings.

DETAILED DESCRIPTION

Figure 1:
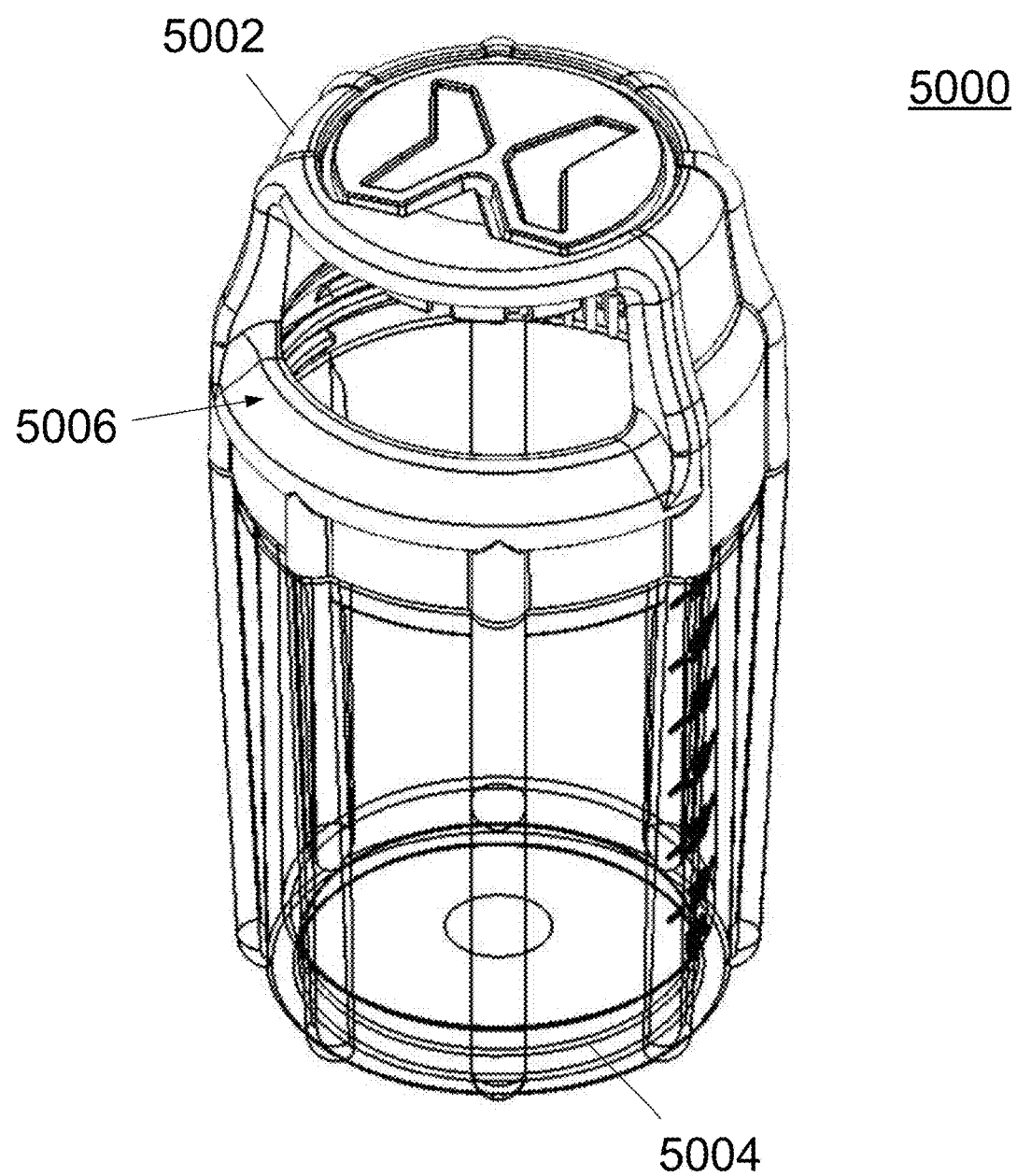
FIG. 1 is a perspective view of a collector used to collect cut bone from a kerrison rongeur in accordance with an embodiment of the present invention.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention in any claim of a patent issuing here from, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112(f), no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Additionally, as used herein, "cap" denotes "a lid configured to be attached to an object in covering relation to an interior containment space of the object".

As used herein, a "scraper" is a brush, a group of bristles, a protuberance, a barb, or a finger; and is sufficiently rigid so as to generally hold form when not engaged by the distal end of a kerrison rongeur and to generally dislodge bone found in a cutting area of a kerrison rongeur when moved into or through the cutting area. Preferably, a scraper also is sufficiently flexible and resilient so as to generally deflect and bend to some extent upon abutment by and engagement with the distal end of a kerrison rongeur. A scraper may be relatively hard or soft within this range. Furthermore, a scraper preferably comprises a bio-absorbable material in at least some embodiments of the invention. In this respect, a scraper may comprise a brush with bio-absorbable bristles which, if inserted into the body, are absorbed by the body.

Figure 1A:
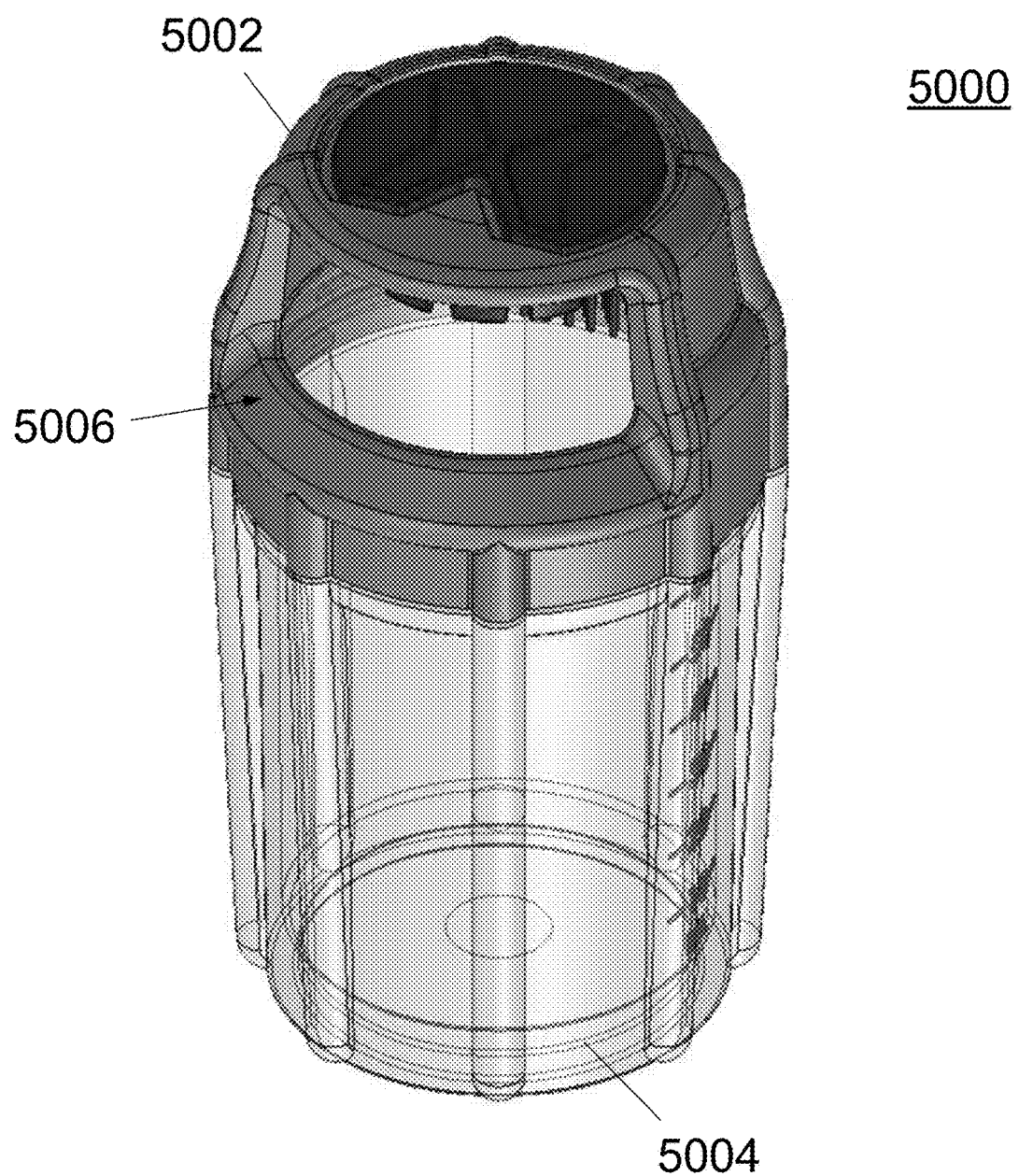
FIG. 1A is a perspective shaded view of the collector of FIG. 1.
Figure 1B:
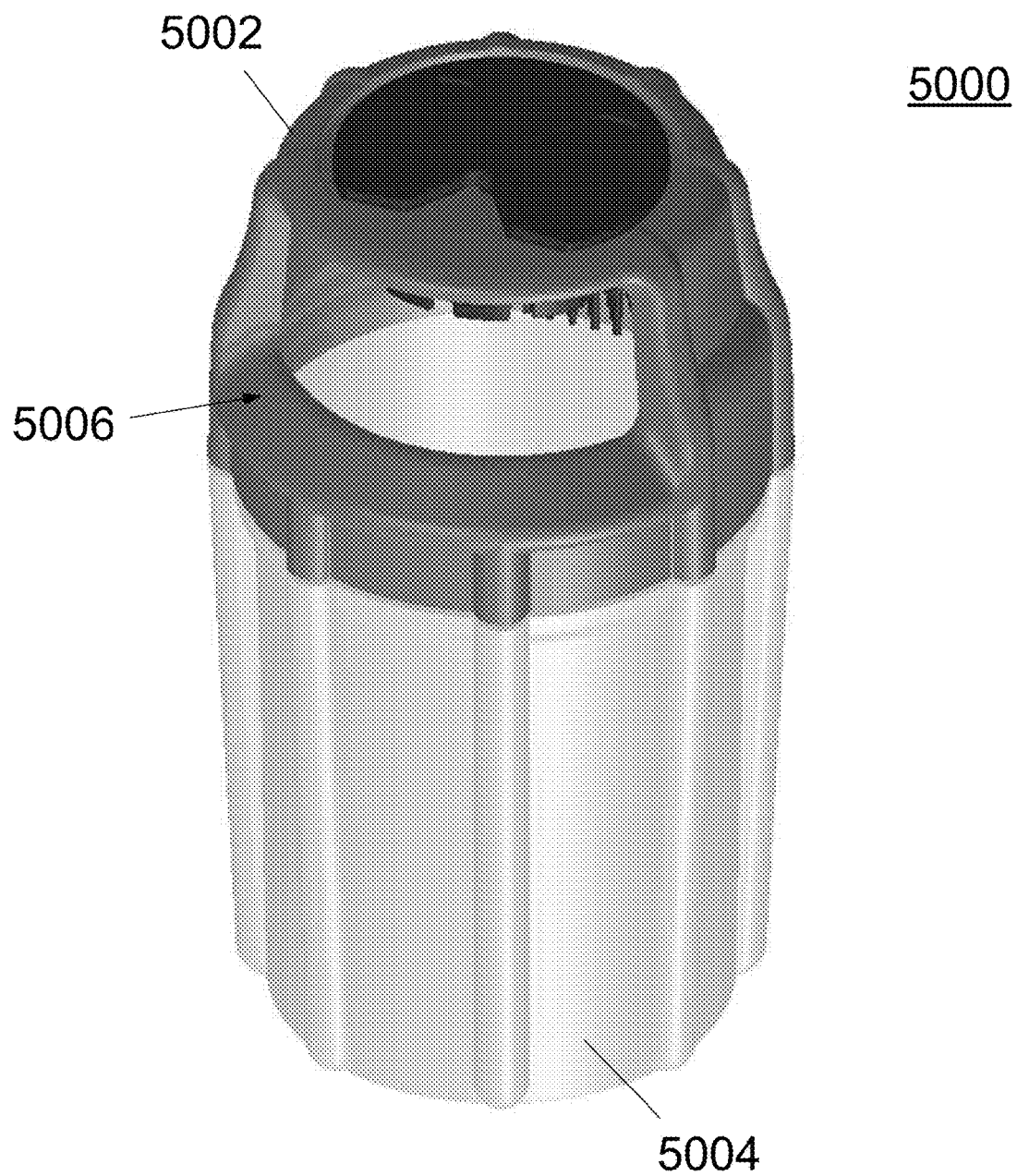
FIG. 1B is another perspective shaded view of the collector of FIG. 1.

As used herein, "kerrison rongeur" denotes a rongeur having a distal end with cutting area as seen in FIGS. 1A and 1B of the '816 Publication, and the phrases "kerrison rongeur" and "kerrison-type rongeur" are intended to be used interchangeably when referring to the present invention.

Referring now to the drawings, one or more preferred embodiments of the present invention are next described. The following description of one or more preferred embodiments is merely exemplary in nature and is in no way intended to limit the invention, its implementations, or uses.

"Bristle Field and Teeth" Preferred Embodiments of the Present Invention

Figure 2:
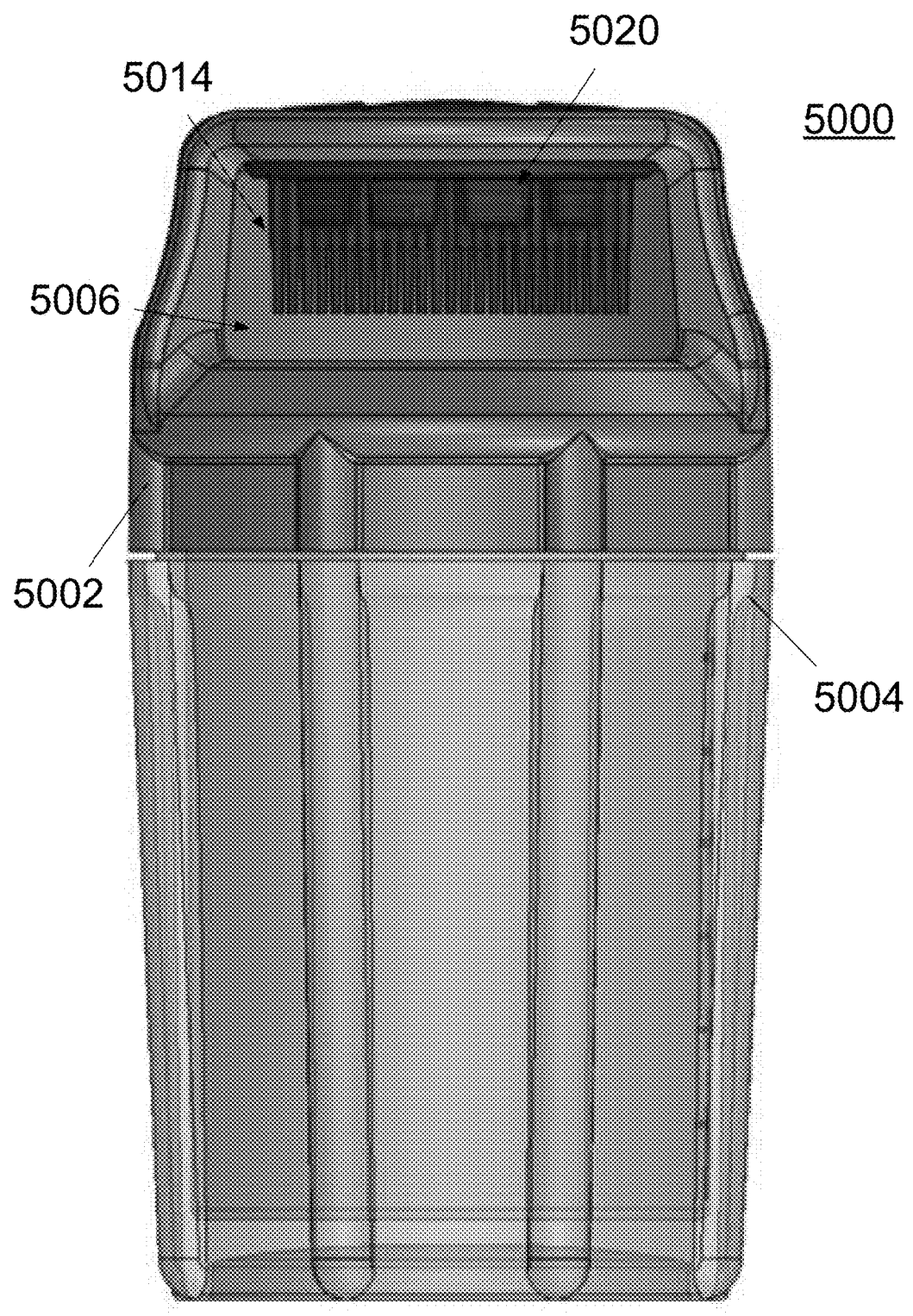
FIG. 2 is a side elevational view of the collector of FIG. 1.

FIG. 1 is a perspective view of a handheld collector 5000 used to collect cut bone from a kerrison rongeur in accordance with an embodiment of the invention. Similarly, FIGS. 1A and 1B are perspective shaded views of the collector 5000, and FIG. 2 is a side elevational view of the collector 5000. As seen in these drawings, the collector comprises a cap 5002 and a container 5004. The cap includes an opening 5006 dimensioned to receive there through a distal end of a kerrison rongeur.

Preferably, the cap is generally circular in perimeter and the opening and extends along an arc having an obtuse angle and, more preferably, the opening extends along an arc having an angle of between 130 degrees and 140 degrees. The container of the collector comprises a generally elongate body that is cylindrical in shape, and walls of the body define an interior containment space 5008 of the container into which bone falls when dislodged from the distal end of the kerrison rongeur.

Figure 3:
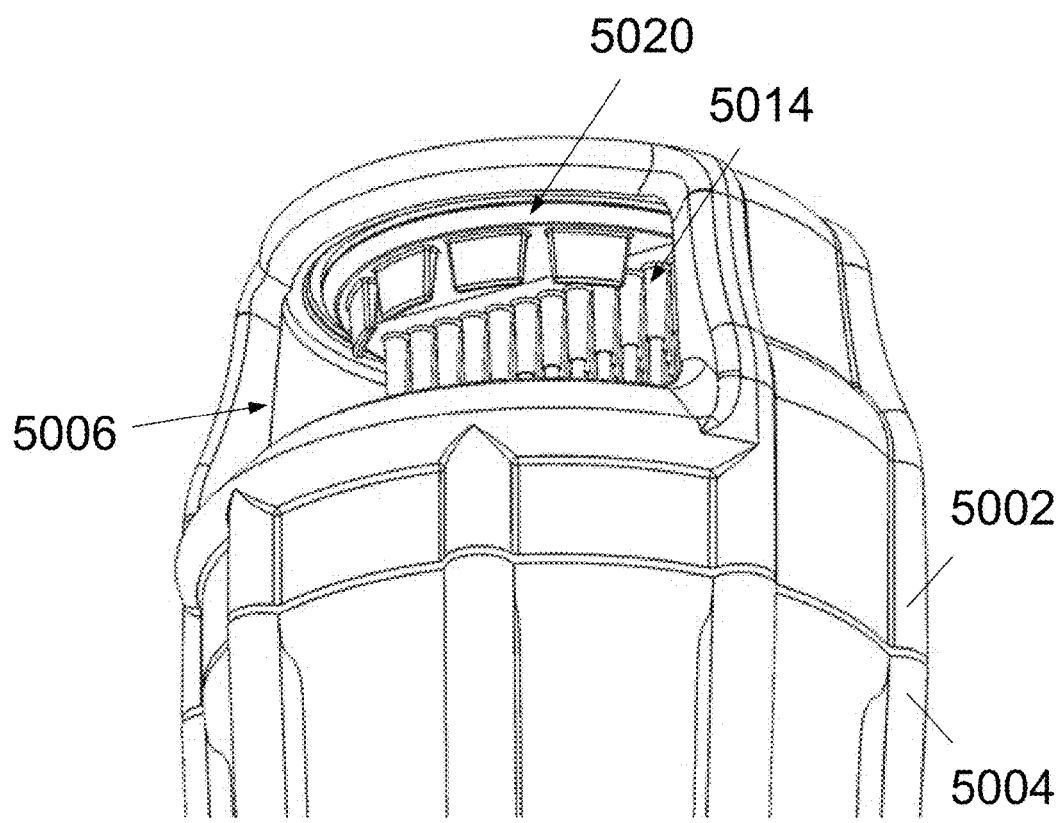
FIG. 3 is a perspective view of an upper portion of the collector of FIG. 1—the upper portion including a cap.
Figure 3A:
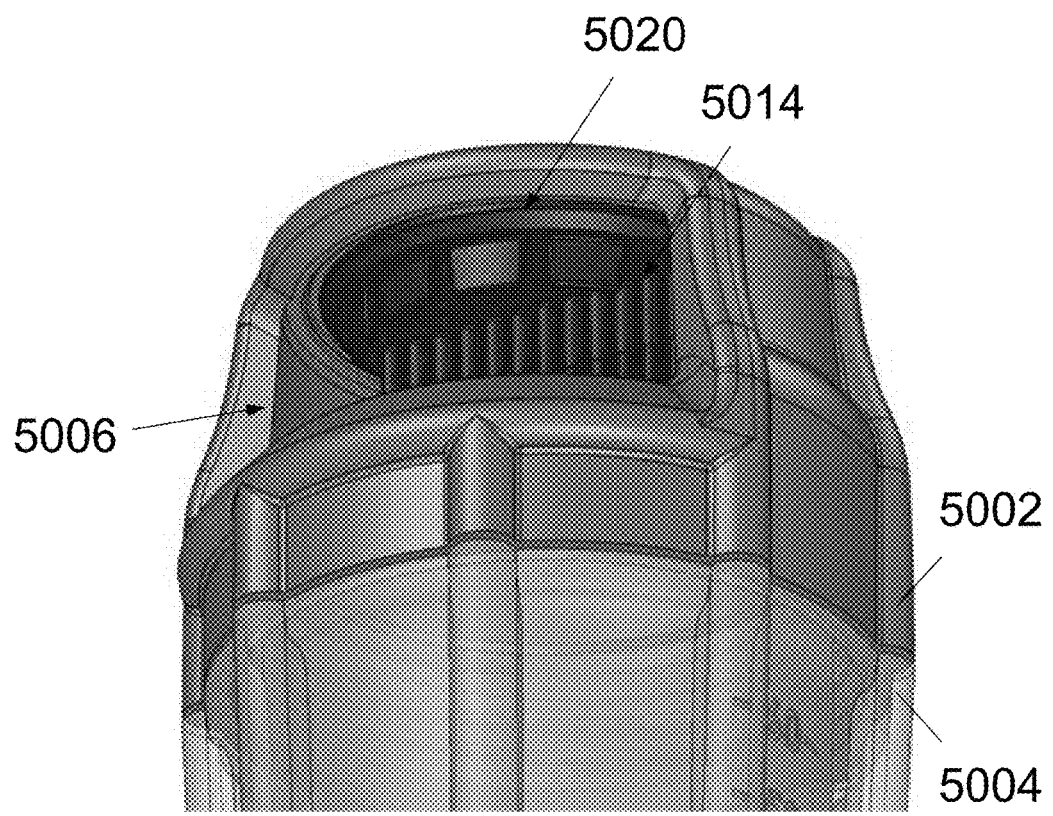
FIG. 3A is a perspective shaded view of the upper portion of the collector of FIG. 1.
Figure 4:
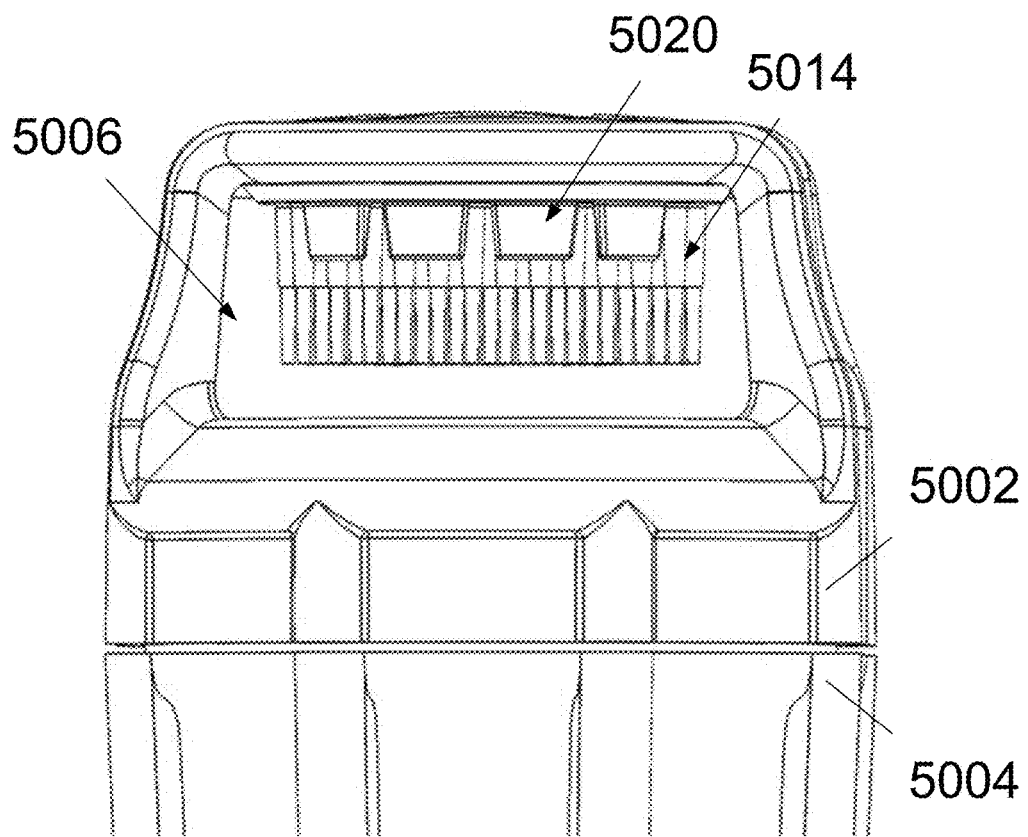
FIG. 4 is a side elevational view of the upper portion of the collector of FIG. 1.
Figure 4A:
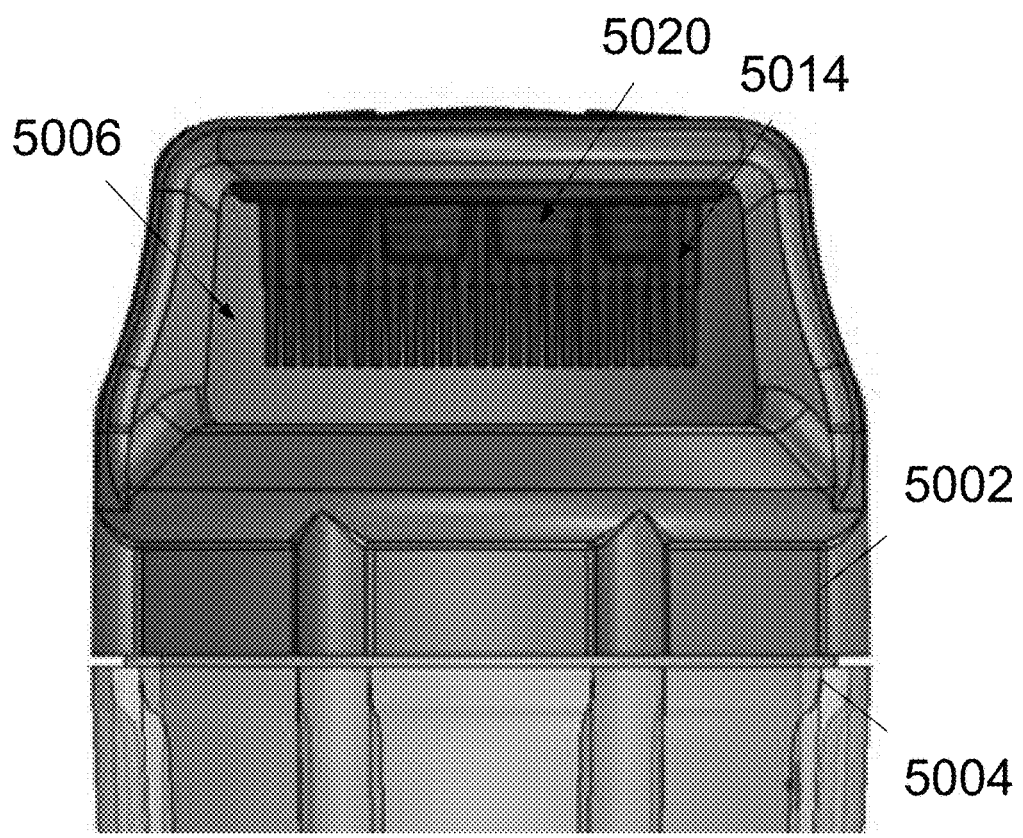
FIG. 4A is a side elevational shaded view of the upper portion of the collector of FIG. 1.

An upper portion of the collector is seen in greater detail in FIGS. 3 and 4 and corresponding shaded views of FIGS. 3A and 4A. In this respect, FIGS. 3 and 3A show a perspective view of the upper portion of the collector including the cap, and FIGS. 4 and 4A show a side elevational view of the upper portion of the collector including the cap.

Figure 5:
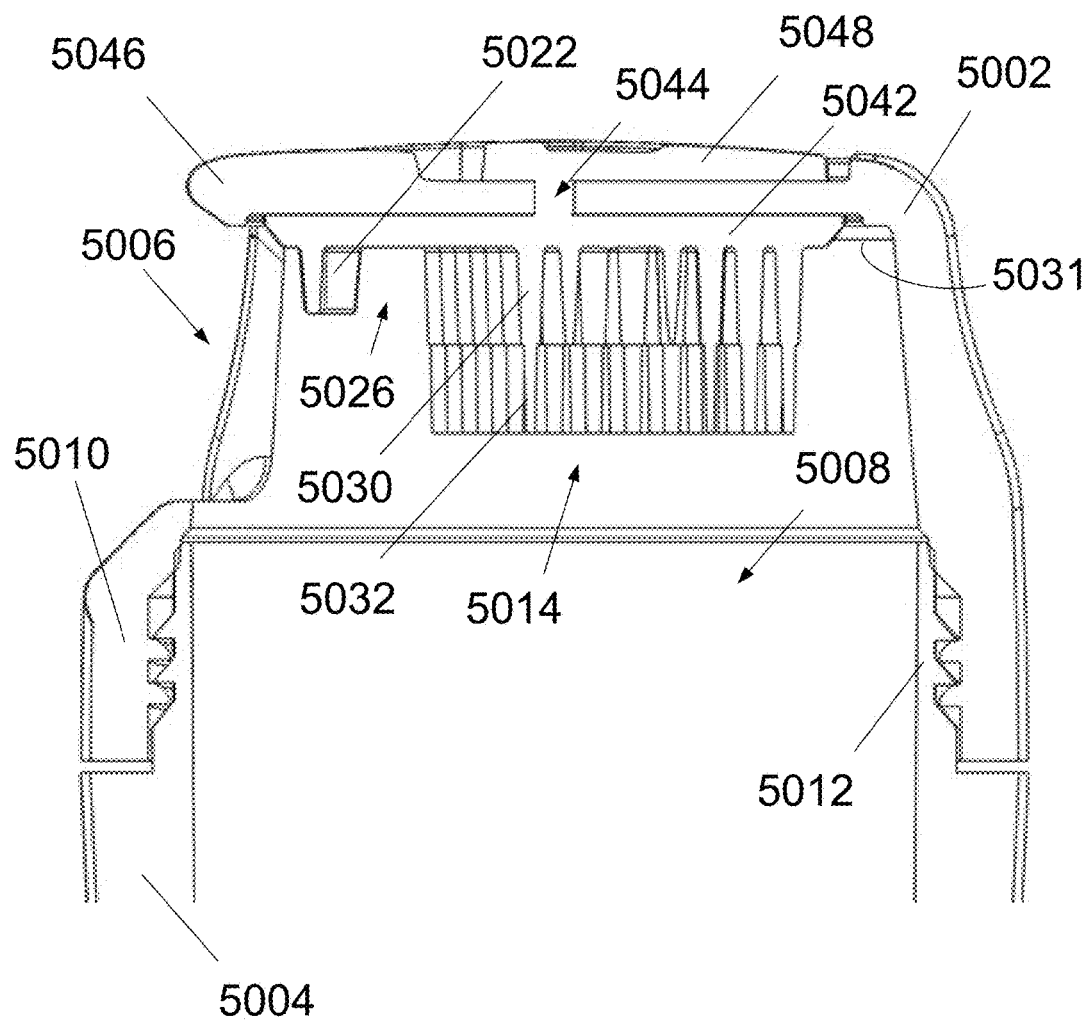
FIG. 5 is a side cross-sectional view of the upper portion of the collector of FIG. 1.
Figure 6:
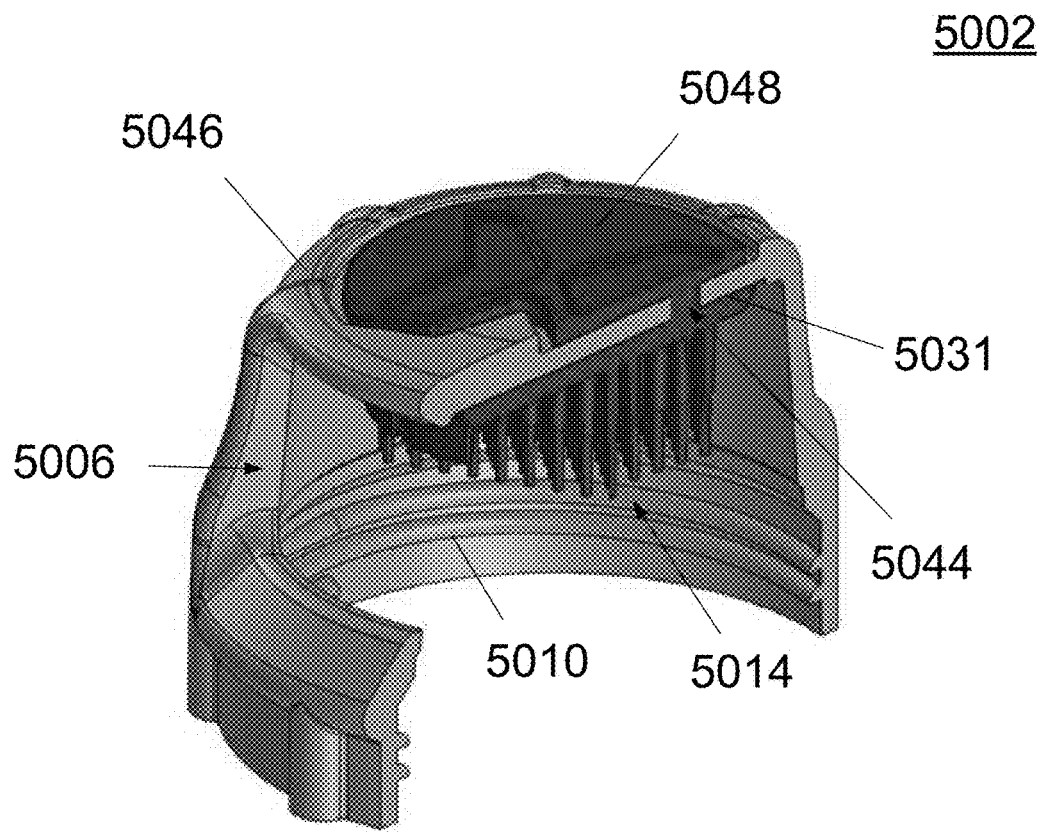
FIG. 6 is a perspective cross-sectional view of the cap of the upper portion of the collector of FIG. 1.
Figure 9:
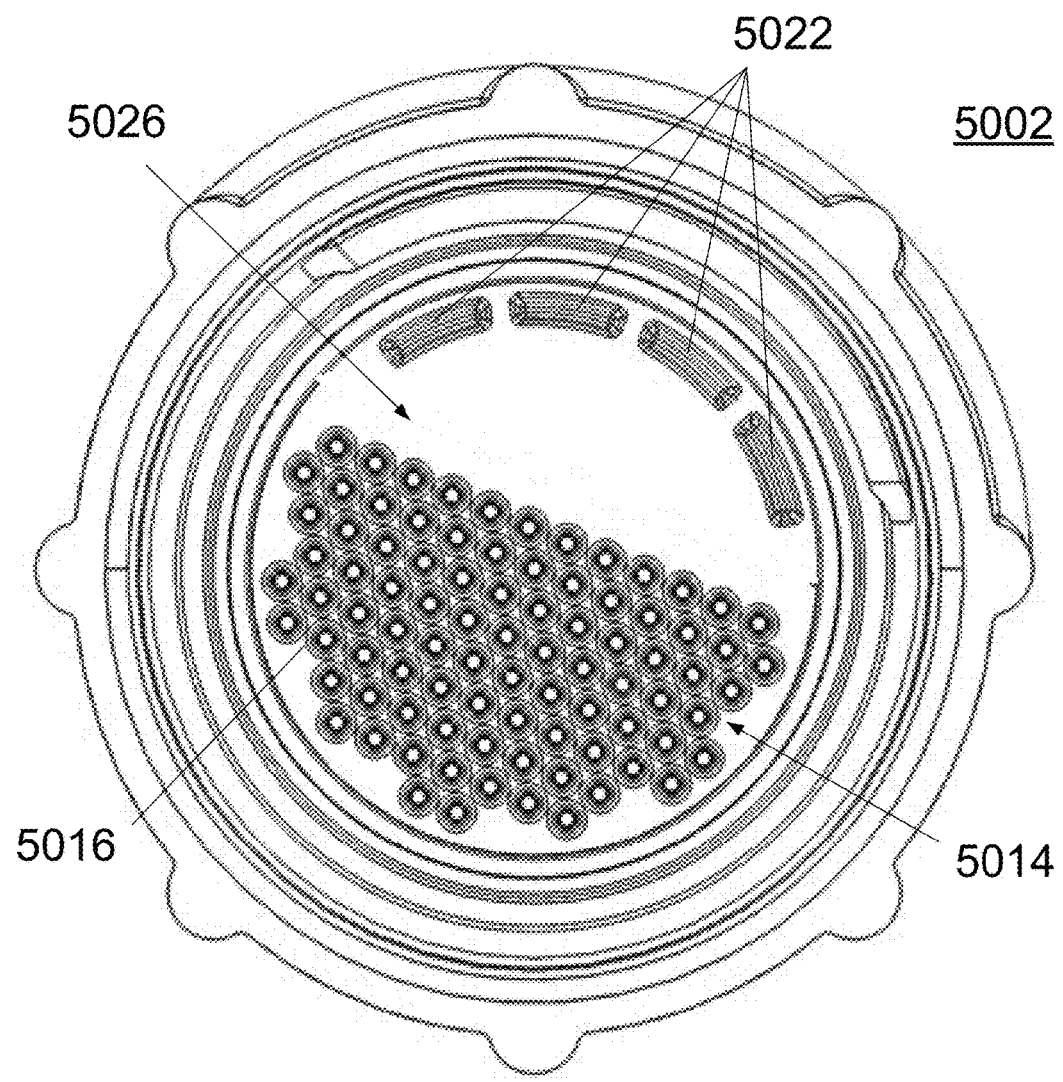
FIG. 9 is a bottom view of the cap of the upper portion of the collector of FIG. 1.
Figure 9A:
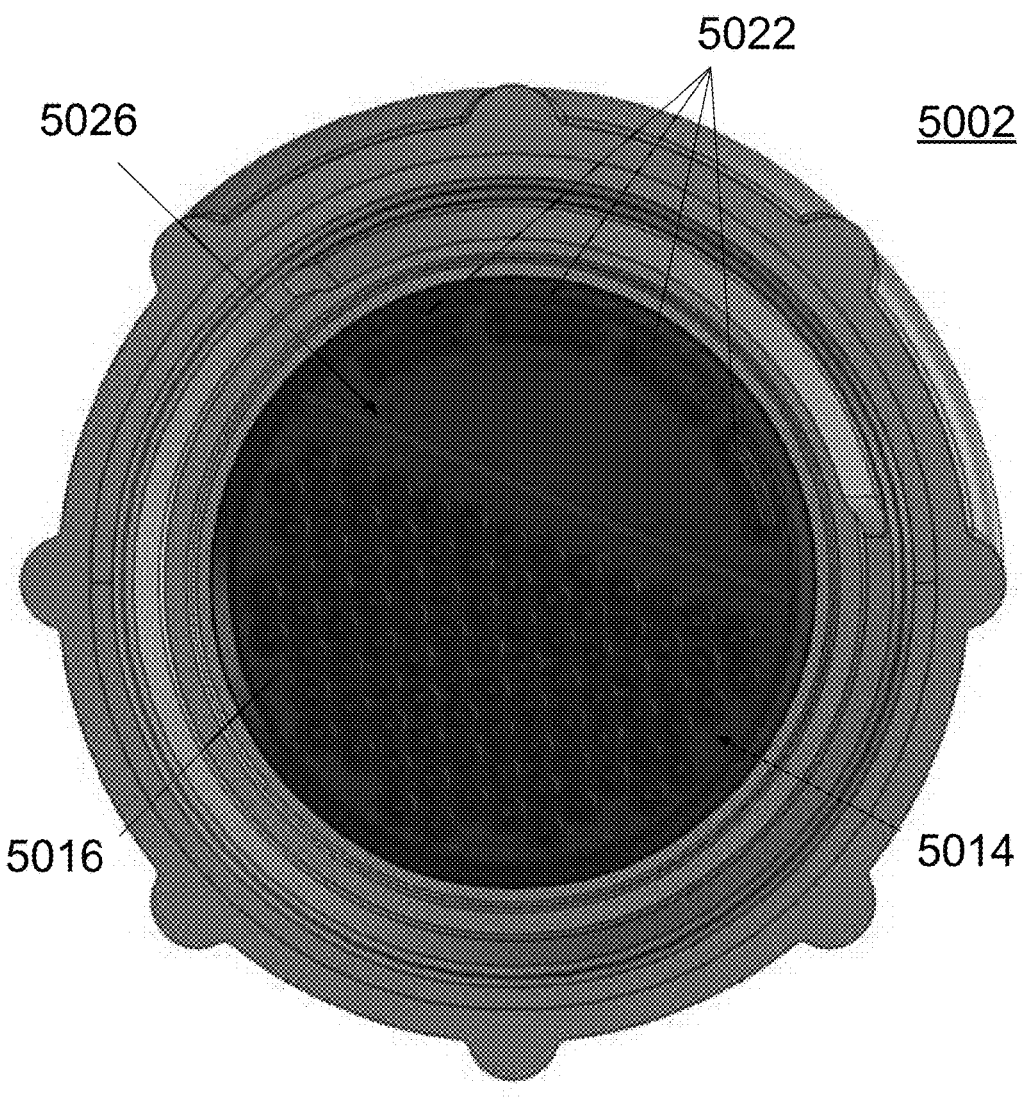
FIG. 9A is a bottom shaded view of the cap of FIG. 9.
Figure 9B:
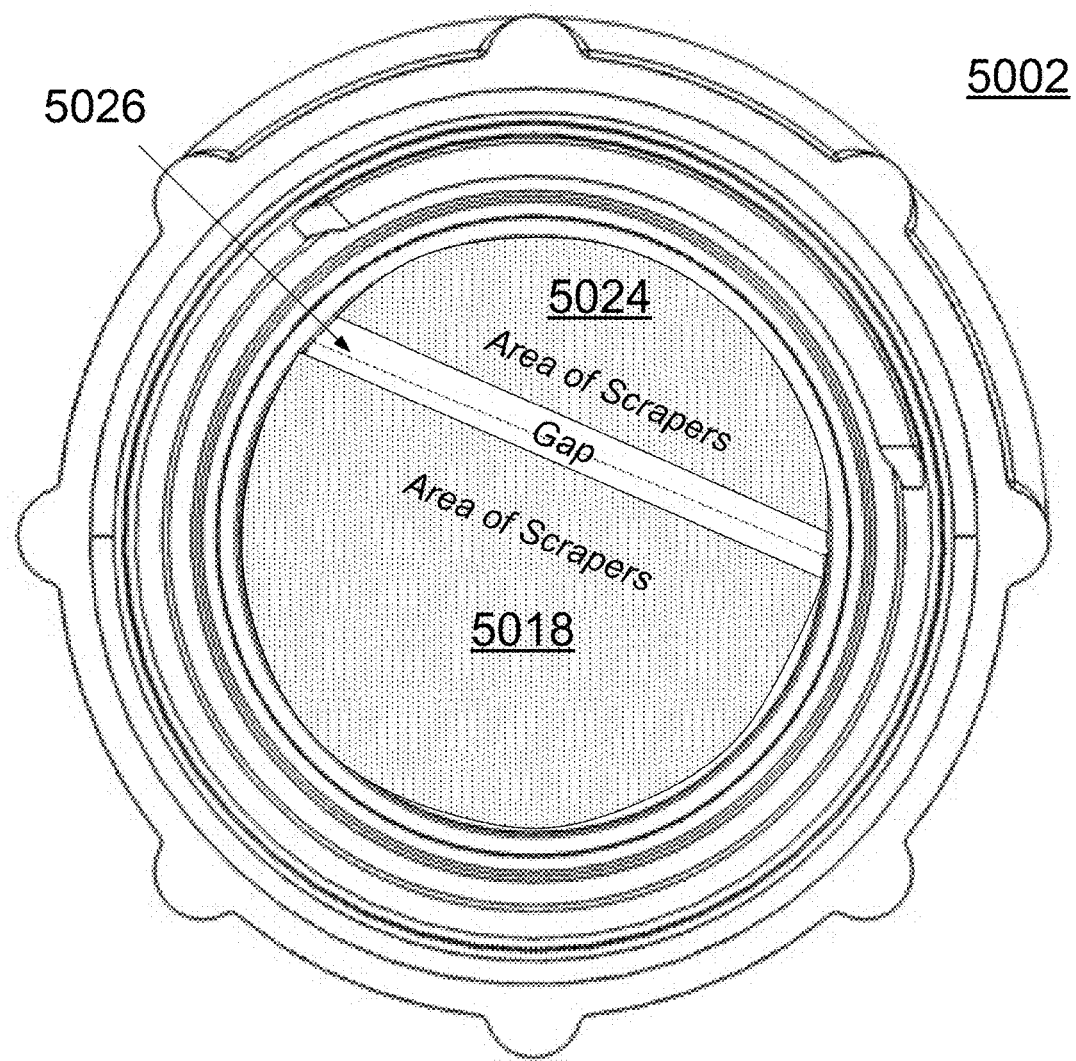
FIG. 9B is a bottom view of the cap of FIG. 7 with areas of different pluralities of scrapers schematically illustrated, including a void or gap that exists between the areas of different pluralities of scrapers.
Figure 10:
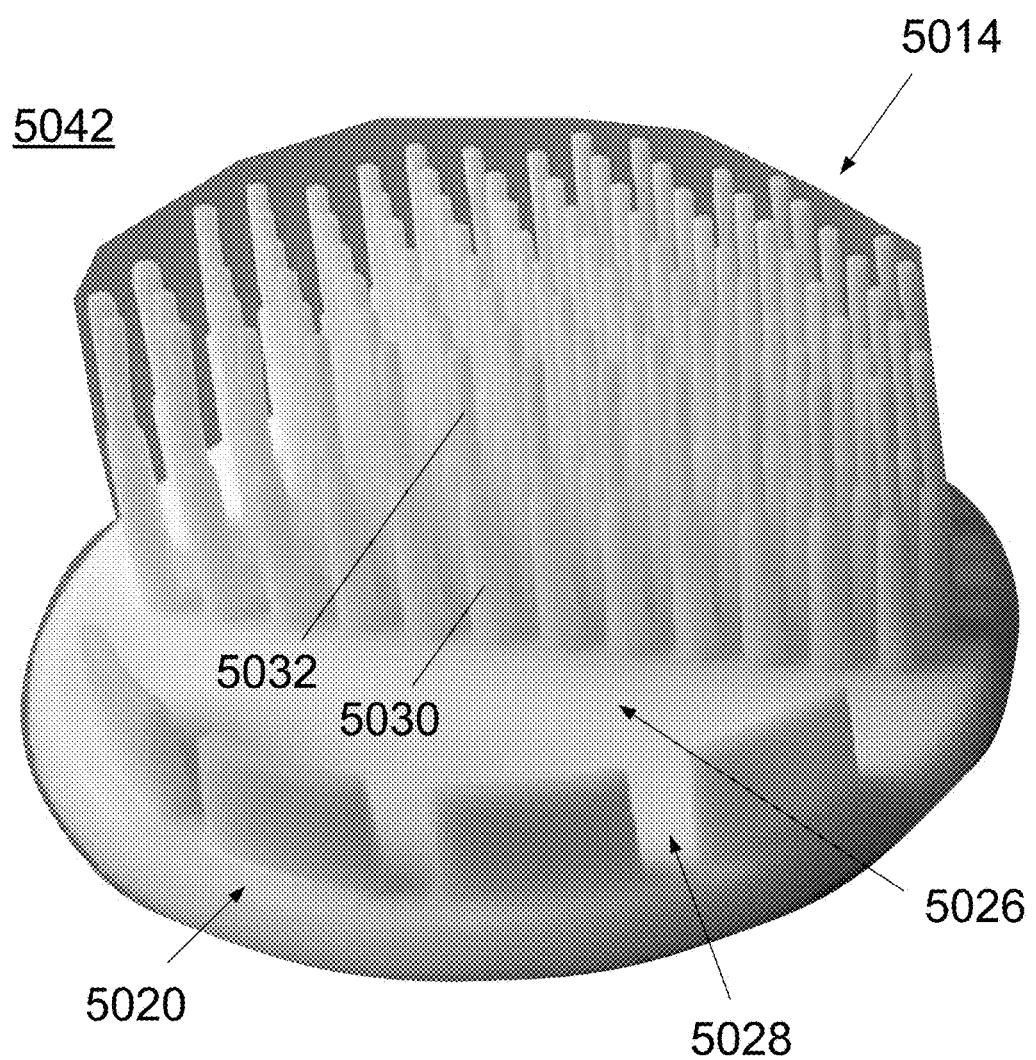
FIG. 10 is a perspective view of a second component of the cap of the upper portion of the collector of FIG. 1.

Additionally, FIG. 5 illustrates a side cross-sectional view of the upper portion of the collector; FIG. 6 is a perspective cross-sectional view of the cap of the upper portion of the collector; and FIG. 9 illustrates a bottom view of the cap of the upper portion of the collector, of which FIG. 9A is a bottom shaded view thereof and 9B is a bottom view thereof schematically illustrating distinct areas of different pluralities of scrapers; and FIG. 10 illustrates a perspective view of a component of the cap of the upper portion of the collector.

As perhaps best seen in FIG. 5, the cap includes a threaded portion 5010 that engages and mates with a threaded portion 5012 of the container when the cap and container are screwed together. The cap is thereby attached to the container in an upper portion of the collector and is removable from the container.

In the preferred collector 5000, the cap includes at least two areas of different pluralities of scrapers for dislodging bone from the distal end of the kerrison rongeur, with a gap extending between the different areas. With particular reference to FIGS. 5, 6, 9, 9A, and 9B, a first plurality 5014 of similar scrapers 5016 is located in a first area 5018 of the underside of the cap that is in close proximity to the opening, and a second plurality 5020 of similar scrapers 5022 is located in a second area 5024 of the underside of the cap that is further from the opening than the first area 5018. Moreover, the first and second areas 5018,5024 are arranged in spaced relation to each other such that a gap 5026 comprising an absence of scrapers extends between the first plurality 5014 and the second plurality 5020.

Referring now to FIGS. 5, 6, 9, 9A, and 9B, each scraper 5016 is seen to comprise a finger insofar as each scraper comprises a protuberance that is elongate with generally oval cross-section. Moreover, each such finger has a stepped diameter between a proximal portion 5030 thereof and a distal portion 5032 thereof relative to the underside 5031 of the cap (FIGS. 5 and 6). In this respect, such finger includes a larger width at the proximal portion and a smaller width at the distal portion. The width of such finger further tapers along the proximal portion, decreasing as a height-wise extent increases away from the underside of the cap. The width of the distal portion similarly may taper, and in variations between different embodiments of the invention the stepped-diameter may be omitted with the finger tapering along its overall height from the underside of the cap to its distal end. In still other embodiments, it is contemplated that the finger may not taper along its height. In any event, the first area 5018 of the first plurality 5014 of scrapers 5016 itself preferably comprises a grouping of these fingers that collectively form a bristle field much like that of a brush.

With continuing reference to FIGS. 5, 6, 9, 9A, and 9B, each scraper 5022 is seen to comprise a wiper having a length and a height that substantially exceeds a width thereof. Moreover, as perhaps best seen in FIG. 9B, the second area 5024 of the second plurality 5020 of such scrapers comprises a grouping thereof collectively forming a row of teeth with each tooth being a wiper and with a gap 5028 extending between adjacent teeth. The row of teeth is arranged along an arc generally extending in close relation to a circumferential boundary of the underside of the cap, perhaps as best seen in FIG. 9. Additionally, preferably one row of teeth is formed; however, it is contemplated that multiple rows of teeth or different arrangements of the teeth may be utilized within the broader scope of the present invention.

In comparison of each scraper 5016 to a scraper 5022, each scraper 5016 in extending from the underside of the cap is more than twice the height of each scraper 5022, which is perhaps best seen in FIG. 5. Indeed, as shown, the height of the lower portion of each scraper 5016 is greater than the height of each scraper 5022.

Each scraper is sufficiently rigid so as to generally hold form when not engaged by a distal end of a kerrison rongeur and to generally dislodge bone found in a cutting area of a kerrison rongeur when the scraper is moved into or through the cutting area. Each scraper also is sufficiently flexible and resilient so as to generally deflect and bend to some extent upon abutment by and engagement with the distal end of a kerrison rongeur. A scraper may be relatively hard or soft within this range.

With respect to the preferred embodiment 5000, each scraper 5022 is less flexible and resilient when compared to the proximal portion 5030 of each scraper 5016; and each scraper 5022 is less flexible and resilient when compared to the distal portion 5032 of each scraper 5016. Furthermore, the proximal portion 5030 of each scraper 5016 is less flexible and resilient when compared to the distal portion 5032 of each scraper 5016. These differences in the flexibility and resiliency characteristics preferably arise from the differences in the relative thicknesses of the scraper 5022, the proximal portion 5030, and the distal portion 5032. The differences also may arise from differences in shape of the scraper 5022, the proximal portion 5030, and the distal portion 5032; from differences in the materials from which the scraper 5022, the proximal portion 5030, and the distal portion 5032 are formed; and any combination of such possibilities.

In the preferred embodiment, each scraper 5022 and the proximal portion 5030 and the distal portion 5032 of each scraper 5016 are all formed from the same material by molding and, preferably, by injection molding. Preferably, these scrapers are integrally formed as a single piece 5042 of the cap 5002, as perhaps best seen in FIG. 5. Additionally, FIG. 10 is a perspective view of the single component.

Figure 7:
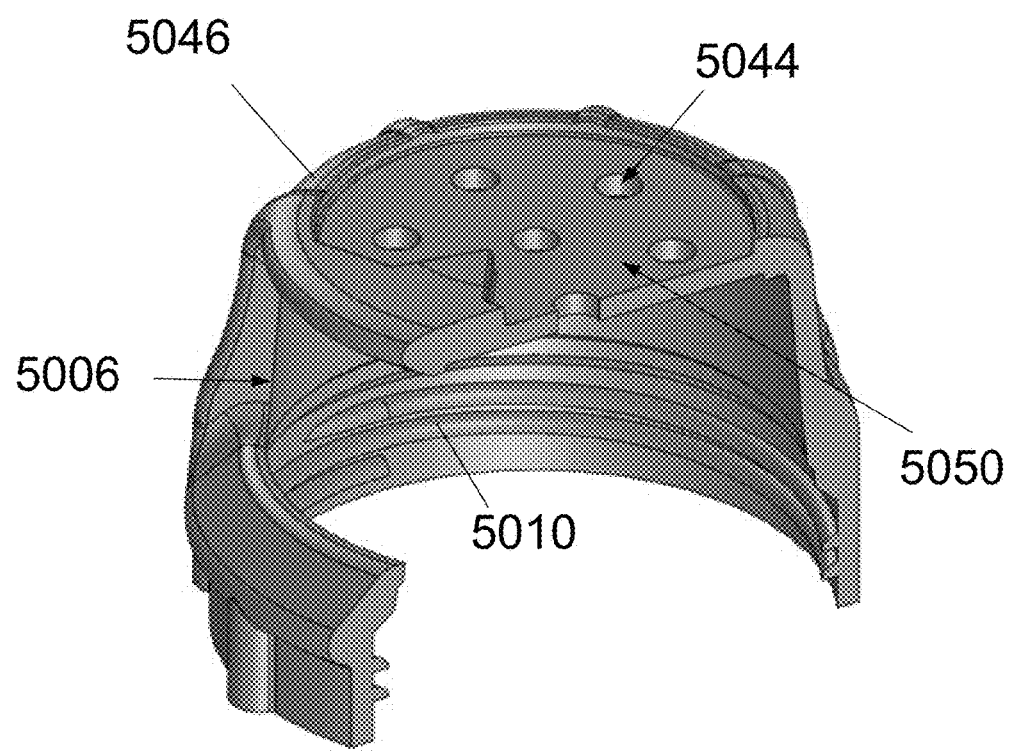
FIG. 7 is a perspective cross-sectional view of a first component of the cap of the upper portion of the collector of FIG. 1.
Figure 8:
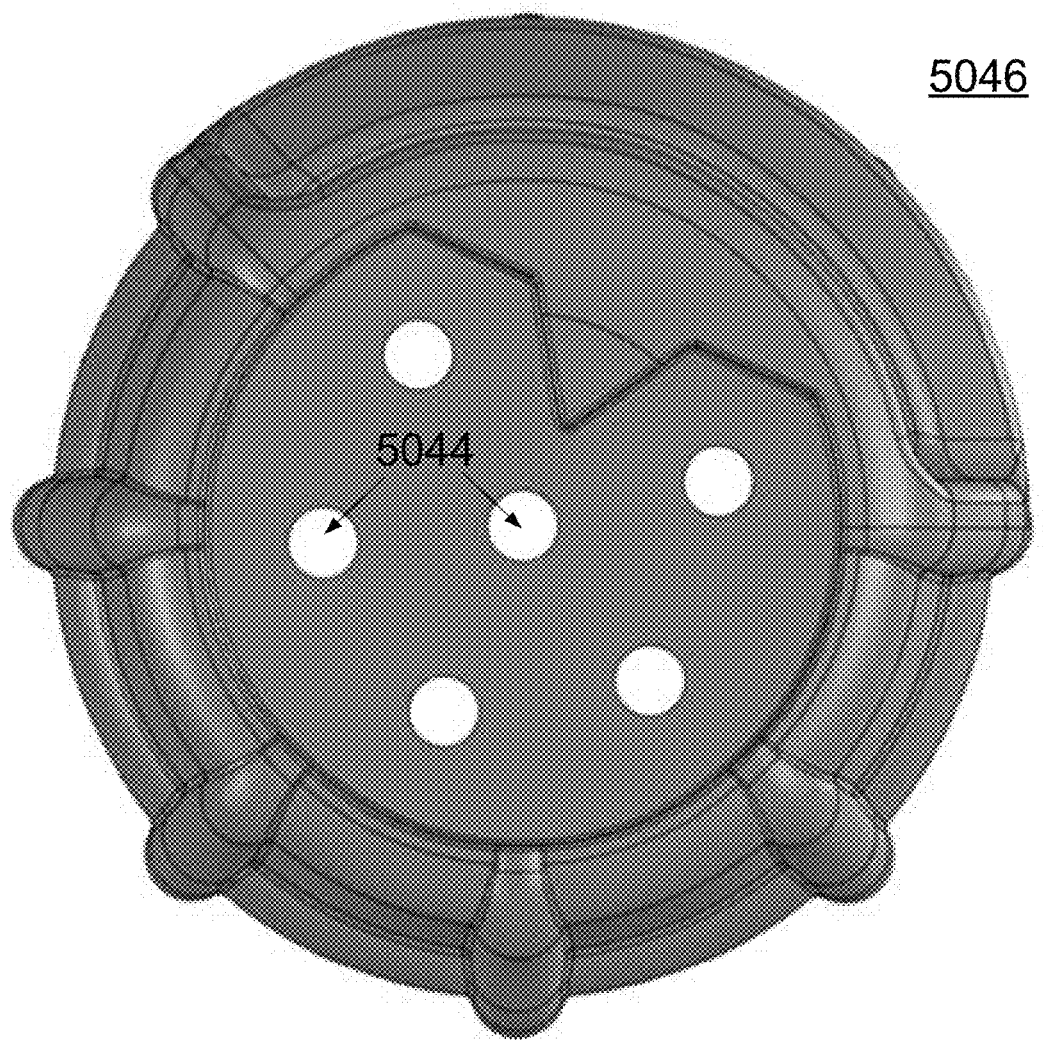
FIG. 8 is a top view of the first component of FIG. 7.

The single component 5042 extends through a plurality of channels 5044 formed in a second, base component 5046 of the cap, to a top surface of the second component 5046, whereat the first component 5042 includes a topside portion 5048. The topside portion preferably is located within a recess 5050 formed in the top surface of the second component 5046 and comprises an ornamentation including branding or a decorative element. FIG. 7 is a perspective cross-sectional view of the second component 5046 of the cap, and FIG. 8 is a top view of this second component 5046.

In manufacturing the collector 5000, the cap 5002 preferably is made by injection molding the first component 5042 on the second component 5046. The second component also preferably is first molded. Thus, one or more of these components and even the container itself may be molded from one or more inert plastic materials, for example. Furthermore, the materials preferably are lightweight such that the collector is readily manipulated by hand for dislodging bone from a distal end of a kerrison rongeur that is received therein. Additionally, the collector may be disposable, insofar as the collector may be used during a single medical procedure for a patient and then discarded in accordance with applicable HAZMAT protocols. Alternatively, one or more components of the collector (including all of the components) may be designed to be—and are able to be—sterilized for reuse with another patient during another procedure.

Still yet in at least some manufacturing methods, the material from which the first component—and specifically the scrapers thereof—is molded also comprises a bio-absorbable material which, if inserted into the body, is absorbed by the body.

By molding—and specifically overmolding—the component including the scrapers on both sides of the base component of the cap as well as through the channels in the base component of the cap, the scrapers are permanently affixed to the base component on the underside of the cap and are not removable from the cap without tearing of the overmolded component. As such, there is no need for assembly of the cap, and it is believed that the risk is reduced that one or more scrapers may become detached during aggressive engagement of the distal end of the rongeur with the scrapers. Such manufacturing method further is believed to protect against other product failures arising from other means of attaching the scrapers within the cap.

Figure 11:
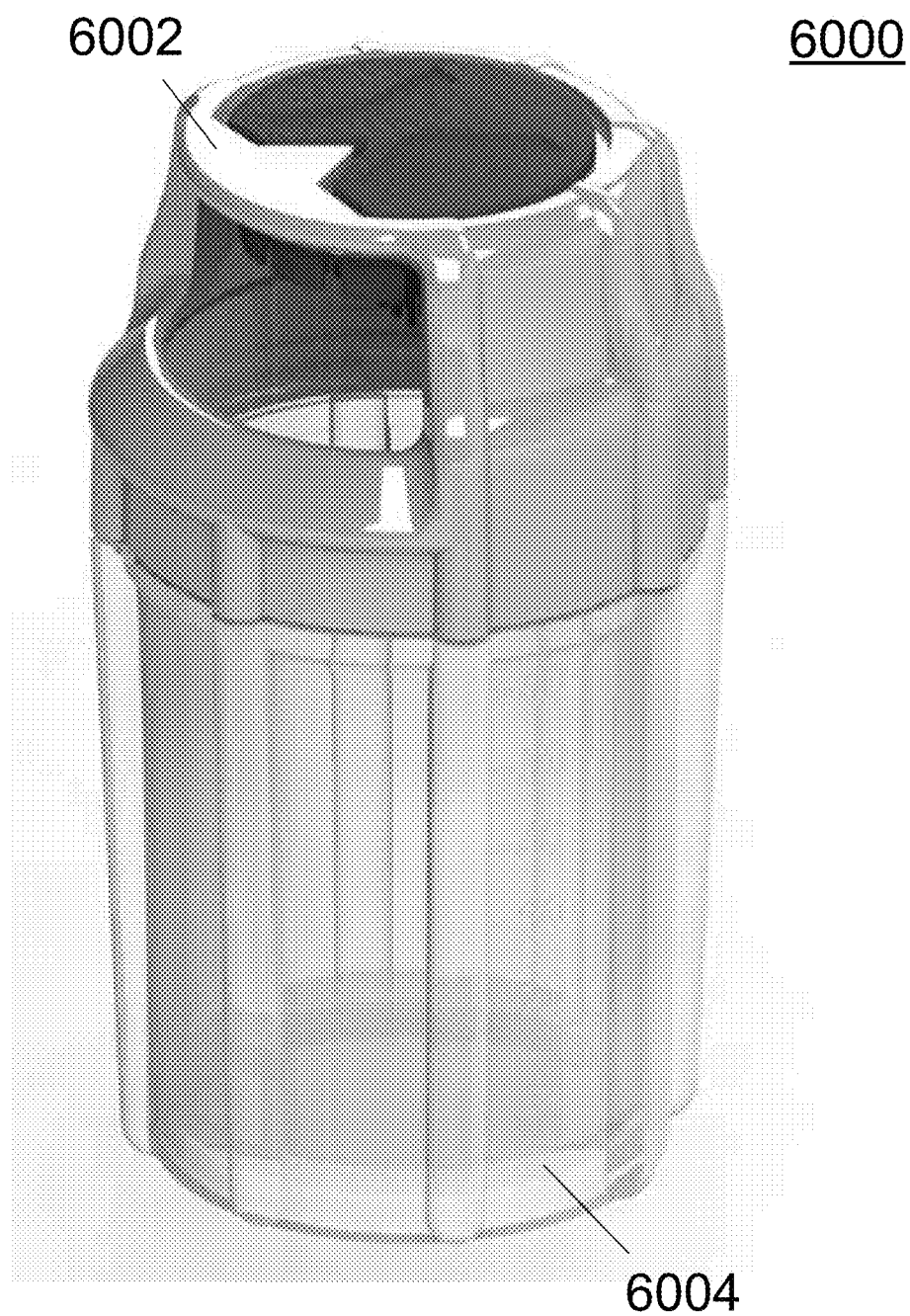
FIG. 11 is a perspective view of a collector used to collect cut bone from a kerrison rongeur in accordance with an embodiment of the present invention.
Figure 12:
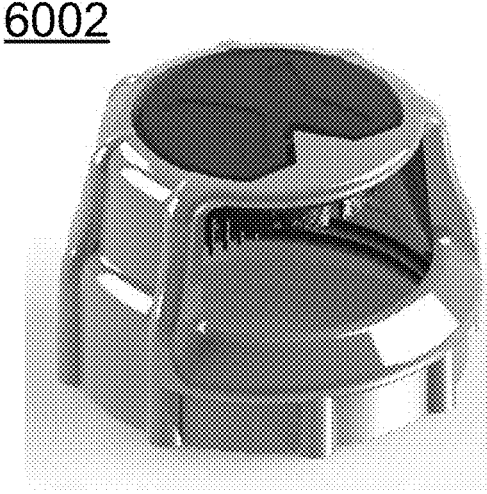
FIG. 12 is a perspective view of a cap of the collector of FIG. 11.
Figure 13:
FIG. 13 is a top view of the cap of FIG. 12.
Figure 14:
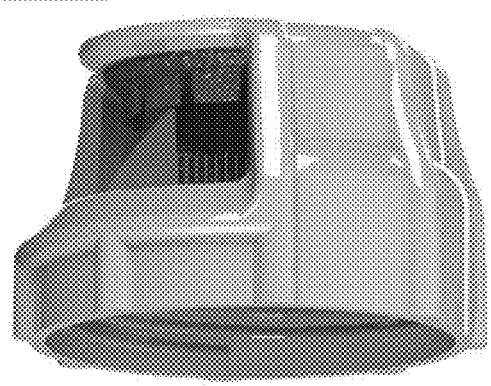
FIG. 14 is a side perspective view of the cap of FIG. 12.
Figure 15:
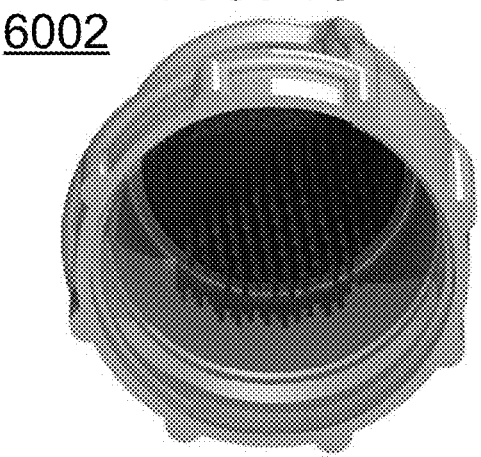
FIG. 15 is a bottom perspective view of the cap of FIG. 12.
Figure 16:
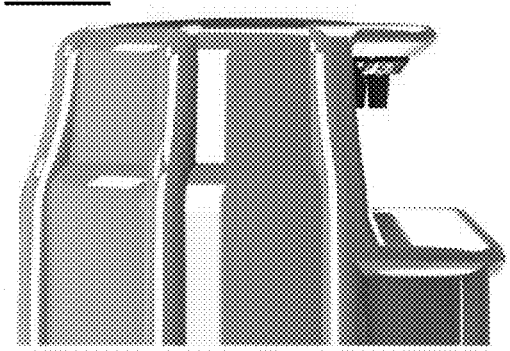
FIG. 16 is a side elevational view of the cap of FIG. 12.
Figure 17:
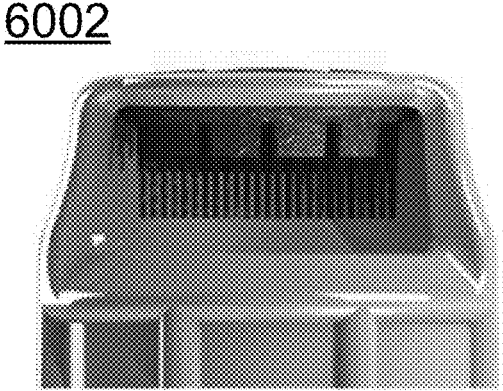
FIG. 17 is another side elevational view of the cap of FIG. 12.
Figure 18:
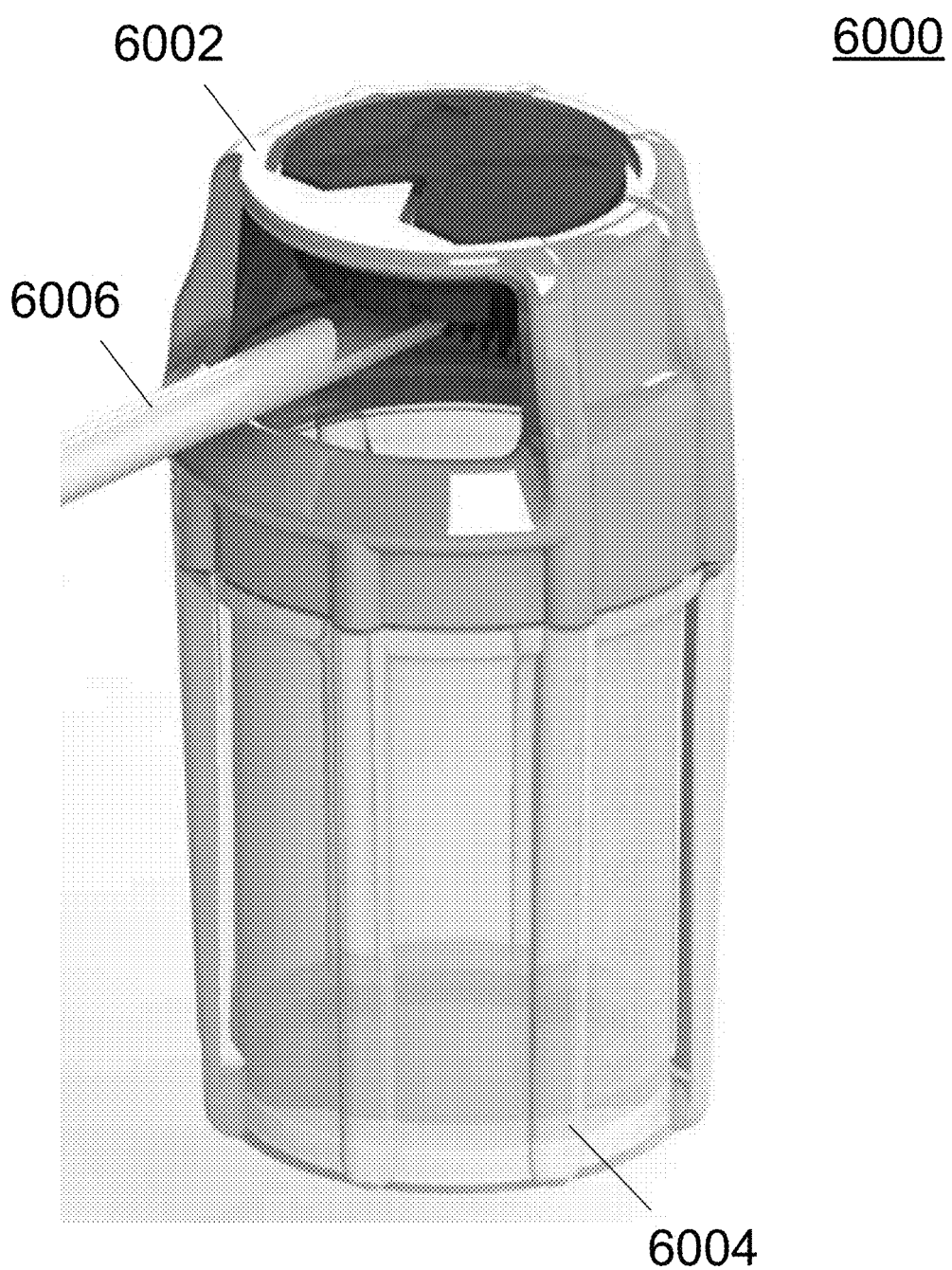
FIG. 18 is a perspective view of the collector of FIG. 11 and portion of a kerrison rongeur 6006 including distal tip thereof which has been inserted into and received within the cap of the collector.

FIG. 11 is a perspective view of a collector 6000 used to collect cut bone from a kerrison rongeur in accordance with another embodiment of the present invention. The collector 6000 is similar in structure to the collector 5000 and includes a cap 6002 and container 6004. FIG. 12 is a perspective view of the cap 6002; FIG. 13 is a top view of the cap; FIG. 14 is a side perspective view of the cap; FIG. 15 is a bottom perspective view of the cap; FIGS. 16 and 17 each is a side elevational view of the cap; and FIG. 18 is a perspective view of the collector 6000 and portion of a kerrison rongeur including distal tip thereof which has been inserted into and received within the cap 6002.

Figure 19:
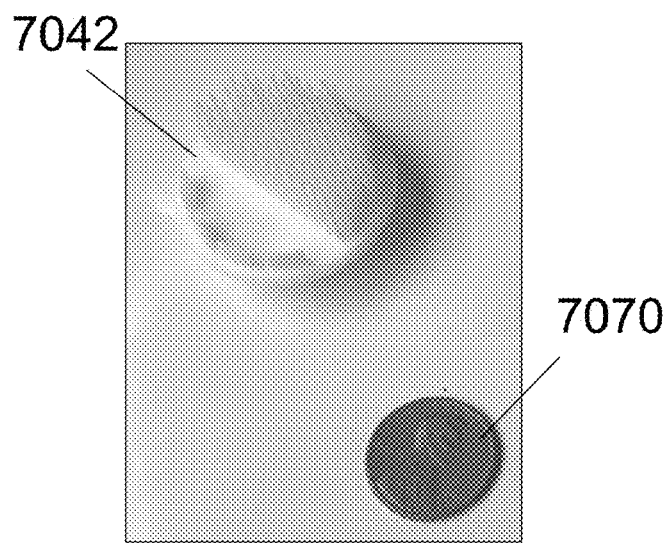
FIG. 19 is a photograph of a representative first component of a cap placed adjacent a penny to demonstrate preferred size.
Figure 20:
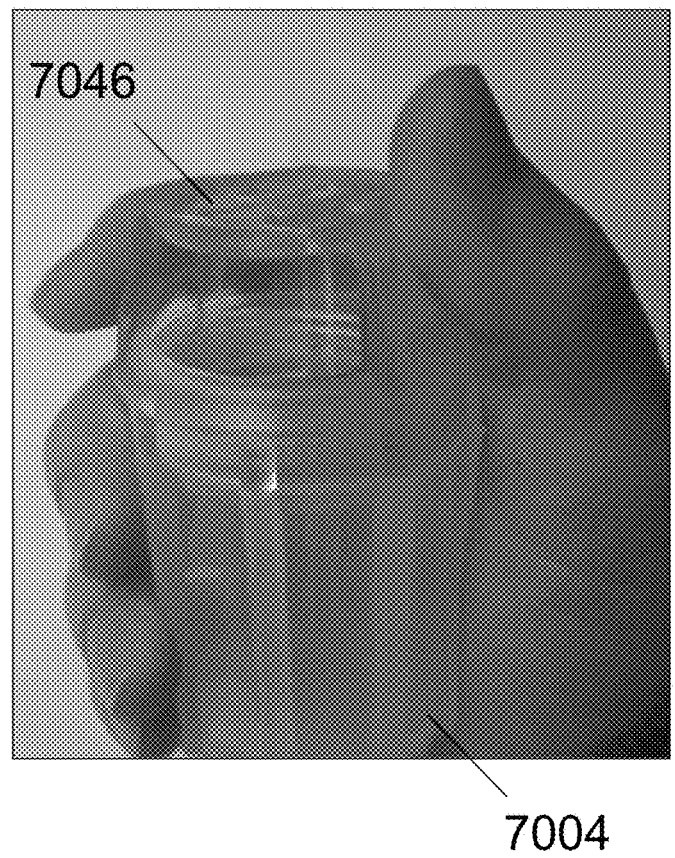
FIG. 20 is a photograph of a representative container being held by hand with a representative second, base component having been screwed onto the container.

To demonstrate relative size, FIG. 19 is a photograph of a representative first component 7042 placed adjacent a penny 7070; and FIG. 20 is a photograph of a representative container 7004 being held by hand with a representative second base component 7046 screwed on the container.

Yet another collector in accordance with another embodiment of the present invention is similar in structure to collectors 5000,6000 and is disclosed in the computer program listing of the appendix, which is incorporated by reference herein.

In view of the foregoing, it will be appreciated that in each of these preferred embodiments represented in FIGS. 1-18, the cap comprises pluralities of scrapers that differ based on flexibility and resiliency as well as arrangement and spacing between adjacent scrapers. Indeed, as seen herein, preferred embodiments each include a first plurality of scrapers shaped and configured in an arrangement to resemble a bristle field like that of a brush, and a second plurality of scrapers shaped and configured in an arrangement to resemble a row of teeth, with the row of teeth extending along the opening and with the bristle field located distal to the opening and with a gap extending between the row of teeth and the bristle field.

From experimentation it has been found that this combination of different plurality of scrapers, i.e., the bristle field and teeth, advantageously removes more bone during use of a collector than the bristle field alone. In particular, it has been found that the method of: inserting the distal end of the rongeur through the opening in the cap, preferably at an angle of 30-40 degrees, and preferably without engaging the teeth; then causing the distal end to engage and be moved and rotated within the bristle field; and, upon withdrawal of the distal end, then engaging the distal end with the teeth, results in a greater amount of bone being dislodged within the container than if the teeth were omitted from the collector.

In accordance with preferred embodiments of the present invention, a patient advantageously is afforded his or her own bone for the fusion when a collector is used to harvest bone cut from the patient using a kerrison rongeur. For example, lamina chips are clinically proven to have both osteoinductive and osteoconductive properties conducive for bone fusion. By using a patient's own bone, there is less chance of rejection, infection, and significant cost by not having to rely on bone substitute.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method of manufacturing a cap for a collector, the cap comprising pluralities of scrapers that differ based on flexibility and resiliency as well as arrangement and spacing between adjacent scrapers, the method comprising:
   providing a base component; and
   injection molding an additional component onto the base component to form the cap, the additional component being molded in a shape defining a first area having a first plurality of scrapers defining a bristle field and a second area having a second plurality of scrapers defining a row of teeth, with a gap comprising an absence of scrapers extending between the first and second areas.

2. The method of claim 1, wherein the method of providing the base component comprises first molding the base component.

3. The method of claim 1, wherein the additional component is overmolded on the base component.

4. The method of claim 1, wherein one or more of the base and additional components are molded from one or more inert plastic materials.

5. The method of claim 1, wherein the material from which the additional component is molded comprises a bio-absorbable material.

6. The method of claim 1, wherein each of the first plurality of scrapers protrude at least twice the extent to which each of the second plurality of scrapers protrude.

7. The method of claim 1, wherein portions of the additional component extend through channels in the base component of the cap, the channels extending between a topside and an underside of the cap.

8. The method of claim 7, wherein first and second portions of the additional component respectively extend on opposite sides of the base component.

9. The method of claim 8, wherein the first portion of the additional component forms the first and second pluralities of scrapers.

10. The method of claim 9, wherein the scrapers are permanently affixed to the base component on the underside of the cap and are not removable from the cap without tearing of the additional component.

11. A method of manufacturing a cap for a collector, the cap comprising pluralities of scrapers that differ based on flexibility and resiliency as well as arrangement and spacing between adjacent scrapers, the method comprising:
   (a) molding a base component; and
   (b) injection molding an additional component onto the base component to form the cap, the additional component being molded in a shape defining a first area having a first plurality of scrapers defining a bristle field and a second area having a second plurality of scrapers defining a row of teeth, with a gap comprising an absence of scrapers extending between the first and second areas;
   (c) wherein the additional component is overmolded on the base component; and
   (d) wherein portions of the additional component extend through channels in the base component of the cap, the channels extending between a topside and an underside of the cap, with first and second portions of the additional component respectively extending on opposite sides of the base component.

12. A method of manufacturing a collector used to collect cut bone, the collector comprising a container body defining an interior containment space for receiving and retaining collected bone and having an open end for access and removal of collected bone from the interior containment space, and a cap for covering relation to the open end of the collector and having an opening for receiving therein a distal end of a kerrison-type rongeur, the cap comprising pluralities of scrapers that differ based on flexibility and resiliency as well as arrangement and spacing between adjacent scrapers, the method comprising:
   providing the container body; and
   providing the cap by
   (a) providing a base component, and
   (b) injection molding an additional component onto the base component to form the cap, the additional component being molded in a shape defining a first area having a first plurality of scrapers defining a bristle field and a second area having a second plurality of scrapers defining a row of teeth, with a gap comprising an absence of scrapers extending between the first and second areas.

13. The method of claim 12, wherein the method of providing the base component comprises first molding the base component.

14. The method of claim 12, wherein the additional component is overmolded on the base component.

15. The method of claim 12, wherein one or more of the base and additional components are molded from one or more inert plastic materials.

16. The method of claim 12, wherein the material from which the additional component is molded comprises a bio-absorbable material.

17. The method of claim 12, wherein each of the first plurality of scrapers protrude at least twice the extent to which each of the second plurality of scrapers protrude.

18. The method of claim 12, wherein portions of the additional component extend through channels in the base component of the cap, the channels extending between a topside and an underside of the cap.

19. The method of claim 18, wherein first and second portions of the additional component respectively extend on opposite sides of the base component.

20. The method of claim 19, wherein the scrapers are permanently affixed to the base component on the underside of the cap and are not removable from the cap without tearing of the additional component.

* * * * *